United States Patent [19]
Forney et al.

[11] Patent Number: 5,750,496
[45] Date of Patent: May 12, 1998

[54] METHOD OF CONTROLLING CRYPTOSPORIDIUM INFECTONS USING PROTEASE INHIBITORS

[75] Inventors: John R. Forney; Shiguang Yang; Mark C. Healey, all of Logan, Utah

[73] Assignee: Utah State University, Logan, Utah

[21] Appl. No.: 695,411

[22] Filed: Aug. 12, 1996

[51] Int. Cl.[6] .................... A01N 37/18; A01N 45/00; A61K 38/00; A61K 31/56

[52] U.S. Cl. ...................... 514/2; 514/168; 514/192; 514/289; 514/358; 514/314; 514/317; 514/431; 514/440; 514/558; 514/559; 514/867; 530/378; 435/4; 435/5; 435/7; 435/184; 435/244; 435/417; 435/450

[58] Field of Search .................... 530/378; 514/2, 514/317, 314, 440, 431, 289, 192, 358, 168, 867, 558, 559; 435/5, 7, 4, 184, 244, 417, 450

[56] References Cited

U.S. PATENT DOCUMENTS

| | | | |
|---|---|---|---|
| 5,106,618 | 4/1992 | Beck et al. | 424/85.8 |
| 5,416,076 | 5/1995 | Casara et al. | 514/46 |
| 5,484,609 | 1/1996 | Ko | 424/470 |
| 5,583,000 | 12/1996 | Ortiz et al. | 435/7.4 |
| 5,614,551 | 3/1997 | Dick et al. | 514/454 |

FOREIGN PATENT DOCUMENTS

| | | |
|---|---|---|
| 2 283 676 | 5/1995 | United Kingdom . |
| WO 95/10527 | 4/1995 | WIPO . |

OTHER PUBLICATIONS

Castagliuolo, et al., Saccharomyces boulardii Protease Inhibits Clostridium difficile Toxin A Effects in the Rat Ileium, Infection and Immunity, vol. 64, No. 12, pp. 5225–5232, Dec. 1996.

Petersen, C., Cellular Biology of Cryptosporidium parvum, Parasitology Today, vol. 9, No. 3, pp. 87–91, 1993.

Adams, et al., "The Effect of Protease Inhibitors on Eimeria Vermiformis Invasion of Cultured Cells", International Journal for Parasitology, vol. 18, No. 5, pp. 683–685, 1988.

Levine, Norman D., The Biology of the Coccidia, Edited by Peter L. Long, University Park Press Baltimore, pp. 1–33, 1982.

Beatty et al., "Kinetics of association of Serine Proteinases with Native and Oxidized α-1-Proteinase Inhibitor and α-1-Antichymotrypsin*", The Journal of Biological Chemistry, vol. 255, No. 9, pp. 3931–3934, May 10, 1980.

Bonnin et al., "Characterization and immunolocalization of an oocyst wall antigen of Cryptosporidium parvum (Protozoa: Apicomplexa)", Parasitology, 103, pp. 171–177, 1991.

Bristow et al., "Inhibition of HIV–1 by modification of a host membrane protease", International Immunology, vol. 7, No. 2, pp. 239–249, 1994.

Carrell et al., "$\alpha_1$-Antitrypsin and the serpins: variation and countervariation", TIBS, pp. 20–24, Jan. 1985.

Chemicon International Inc., "Human Alpha–1–Antitrypsin Purified Protein", package insert (1 page).

Cohen et al., "Arresting Tissue Invasion of a Parasite by Protease Inhibitors Chosen with the Aid of Computer Modeling", Biochemistry, vol. 30, No. 47, pp. 11221–11229, 1991.

"Correspondence", AIDS, vol. 8, No. 4, pp. 555–556, 1994.

Gellin et al., "Coccidian Infections in Aids", Medical Management of Aids Patients, vol. 76, No. 1, pp. 205, 216–222, Jan. 1992.

Goodgame et al., "Intestinal Function and Injury in Acquired Immunodeficiency Syndrome–Related Cryptosporidiosis", Gastroenterology, vol. 108, No. 4, pp. 1075–1082, Apr. 1995.

Mifsud et al., "Respiratory cryptosporidiosis as a presenting feature of AIDS", Letters to the Editor, pp. 227–228, Aug. 1993.

Miles, "$Alpha_1$–Proteinase Inhibitor (Human)", package insert, pp. 1–8, May 1994.

Modha et al., "Complex formation of human alpha–1–antitrypsin with components in Schistosoma mansoni cercariae", Parasite Immunology, vol. 16, No. 8, pp. 447–450, Aug. 1994.

North, M.J., "The Characteristics of Cysteine Proteinases of Parasitic Protozoa", Bio. Chem., vol. 373, pp. 401–402, Jul. 1992.

O'Donoghue, Peter J., "Cryptosporidium and Cryptosporidiosis in Man and Animals", International Journal for Parasitology, vol. 25, No. 139, 154–155, 165–169, 1995.

Okhuysen et al., "Arginine Aminopeptidase, an Integral Membrane Protein of the Cryptosporidium parvum Sporozoite", Infection and Immunity, pp. 4667–4669, Oct. 1994.

Petersen, Carolyn, "Cryptosporidiosis in Patients Infected with Human Immunodeficiency Virus", Clinical Infectious Diseases, 1992:15 (Dec.); pp. 903–904.

Phillips et al., "Cryptosporidium, chronic diarrhoea and the proximal small intestinal mucosa", Gut, 4 pages, Aug. 1992.

Potempa et al., "The Serpin Superfamily of Proteinase Inhibitors: Structure, Function, and Regulation*", The Journal of Biological Chemistry, vol. 269, No. 23, pp. 15957–15960, Jun. 1994.

Roose et al., "Synthetic protease inhibitors: Promising compounds to arrest pathobiologic processes", J. Lab. Clin. Med., vol. 125, No. 4, pp. 433–439, Apr. 1995.

Travis et al., "Human Plasma Proteinase Inhibitors", Ann. Rev. Biochem., 52:655, 658–675, 1983.

Primary Examiner—Cecilia J. Tsang
Assistant Examiner—Jennifer Harle
Attorney, Agent, or Firm—Trask, Britt & Rossa

[57] ABSTRACT

A method for controlling infections caused by Cryptosporidium parvum. The method comprises using protease inhibiting compounds, preferably serine protease inhibitors, to inhibit excystation, invasion, and parasite maturation and development. The method is directed to therapeutic treatment of mammals, such as humans, exposed to C. parvum, and additionally as a prophylactic treatment in immunocompromised subjects at high risk for contracting cryptosporidiosis.

20 Claims, No Drawings

METHOD OF CONTROLLING CRYPTOSPORIDIUM INFECTONS USING PROTEASE INHIBITORS

TECHNICAL FIELD

The present invention relates to anti-protozoal therapy generally, and more specifically to a method of controlling infections caused by *Cryptosporidium parvum* (*C. parvum*) using protease inhibitors.

BACKGROUND ART

*C. parvum* is a coccidian protozoan that infects the epithelial cells lining the digestive and respiratory tracts of mammals. The protozoan preferentially invades the epithelial cells lining the microvilli lining the small intestine, but all sites of the gastrointestinal tract (including the esophagus, stomach, colon, common bile duct, gall bladder, liver, rectum, and pancreatic duct) can be involved. The most common clinical manifestations of the resulting infection, commonly called cryptosporidiosis, are characterized by voluminous watery diarrhea, cramping abdominal pain, and weight loss. Nausea, vomiting, fatigue, headache, and myalgia may also be present. In immunocompetent individuals, the infection causes a generally self-limited diarrhea and results in spontaneous eradication of the parasite from the intestinal mucosa and a protective acquired immunity. Severe consequences of cryptosporidiosis however can occur in hosts with immature or deficient immune systems. These include young children (usually under five years old), patients undergoing immunosuppressive drug therapy, geriatric hosts having decreased immune responsiveness, and patients with congenital or acquired immunodeficiencies (e.g. Human Immunodeficiency Virus ("HIV") infected and Acquired Immunodeficiency Syndrome ("AIDS") patients). These individuals frequently develop a profuse, protracted diarrheal illness which progresses to a chronic infection of the intestinal epithelium and, potentially, cryptosporidial dissemination into the alveolar and tracheal epithelium.

At present, notwithstanding the fact that more than 120 different compounds have been tested, no effective treatment for cryptosporidiosis in man or animals has been disclosed. Most attempts at conventional chemotherapy with antiparasitic, antifungal, antibiotic or antiviral agents have been unsuccessful. Several colostrum preparations have also been used to treat infections, the best results being obtained with hyperimmune bovine colostrum harvested from dairy cows vaccinated with *C. parvum* antigens. Treatment of protozoal gastrointestinal disorders of parasitic protozoan origin by administration of hyperimmune milk products is disclosed in U.S. Pat. No. 5,106,618 (Apr. 21, 1992) to Beck et al. Despite promising indications, considerable variation has been observed in the therapeutic efficacies of different colostrum preparations. As a result, current treatments center around palliative remedies in addition to treatment with antidiarrheal compounds and fluid and electrolyte replacement to alleviate the dehydration accompanying diarrheal illness.

Maintenance of homeostasis in tissues requires regulation of proteases (proteolytic enzymes) by endogenous protease inhibitors, which form complexes with and achieve selective inactivation of the proteases. Several classes of protease inhibitors, found primarily in blood plasma, exist. One family of such endogenous protease inhibitors, the "serine protease inhibitors" ("serpins"), is comprised of a number of structurally similar proteins. The reactive center of a serpin molecule consists of a reactive site loop structure that binds to the active site of a cognate target enzyme. The resulting serpin:enzyme complex is covalently stabilized as a 1:1 molecular complex under physiological conditions. Synthetic, non-protein based inhibitors are also known and are thought to interact with their target proteases to achieve the same effect.

Protease activity has been described in the invasion, infectivity and pathogenicity of several parasites having structural and invasive characteristics similar to cryptosporidiosis. Protease-mediated events reportedly facilitate the process of host cell attachment in *Eimeria vermiformis* and *Trichomonas vaginalis* infections. Adams, J. H. & G. R. Bushell, *International Journal for Parasitology*, 18:683–685 (1988); Arroyo, R. & Aldrete J., *Infection and Immunity*, 57:2991–2997 (1989). Biochemical properties of sporozoans, such as *Eimeria tenella* and *Plasmodium knowlesi*, which appear to include one or more protease-dependent mediated steps in the host cell adhesion and invasion process have likewise been described. Fuller, A. & McDougald, L., *Journal of Parasitology*, 76:464–467 (1990); Hadley et al., *Experimental Parasitology*, 55:306–311 (1983). Proteinases are also known to affect the maturation and development stages of Leshmania, Trypanosoma, and Giardia. McKerrow et al., *Annual Reviews in Microbiology*, 47:821–853 (1993). Additionally, protease-mediated events that facilitate tissue migration, that degrade host proteins for subsequent use as a source of nutrition, and that provide a potential mechanism for parasites to elude host immune responses have been described in previous publications.

More specifically, several investigators have reported a putative role for surface expressed glycoproteins or lectin-associated membrane affinity to aid in the initial attachment of *C. parvum* sporozoites to host cells. Bonnin et al., *Parasitology* 103:171–177 (1991); Mitschler et al., *Journal of Eukaryotic Microbiology* 41:8–12 (1994); Petersen, C., *Clinical Infectious Diseases* 15:903–909 (1992); Tilley, M. & Upton, S., *FEMS Microbiology Letters* 120:275–278 (1994). It is believed that the initial adherence of sporozoites to host cell membranes may facilitate the spatial orientation of parasite proteases that further enhance cell attachment and, potentially, contribute to the parasite's unique intramembranous location within infected cells.

None of these aforementioned references and publications, however, is believed to disclose or suggest the use of protease inhibitors as a method of/for controlling or preventing infections caused *C. parvum.*

DISCLOSURE OF THE INVENTION

The present invention relates to a method of controlling or preventing infections caused by *C. parvum* using protease inhibitors. Preferably, a method of treating or preventing infections caused by *C. parvum* using serine protease inhibitors. Even more preferably, the present invention relates to a method of controlling *C. parvum* infections using pharmaceutically effective amounts of alpha-1-antitrypsin, antipain, aprotinin, leupeptin, soybean trypsin inhibitor, phenylmethylsulfonyl flouride, or combinations thereof.

BEST MODE OF THE INVENTION

The invention comprises administration of a protease-inhibiting compound (or compounds) to control infections caused by *C. parvum*. Administration of protease-inhibiting compounds are believed to inhibit various protease-dependent mechanisms, such as, parasite attachment, parasite nutrition, excystation, parasite invasion, and parasite maturation and development. As will be apparent from the hereinafter described Examples, protease inhibitors administered as described herein cause a significant reduction in the infectivity of *C. parvum*.

The term "animal" is intended to mean, for the purpose of this invention, any living creature including mammals (e.g. humans, domestic animals, farm animals, and wild animals). The term "gastrointestinal disorder" as used herein means infections relating to the stomach, intestine, gall bladder, and/or biliary tract of a mammal that result in a disturbance of the same in terms of function, structure, or both.

The terms "treating" and "treatment" are intended to mean the amelioration or complete elimination of the symptoms of the disorder and/or the pathogenic origin of the disorder, as part of therapeutic or prophylactic therapy. The term "administer" is intended to mean that any method of treating a subject with a substance, such as orally, intravenously, intramuscularly, subcutaneously, topically, rectally, or via inhalation therapy.

The protease inhibitors of the present invention can be used in the therapeutic and prophylactic treatment of cryptosporidiosis in immunocompromised animals. The most severe consequence of *C. parvum* infection occurs in patients with human immunodeficiency virus where current medical intervention is commonly limited to the palliative treatment of symptoms such as diarrhea, cramping abdominal pain, weight loss, nausea, vomiting, fatigue, headache, and myalgia. Thus, prophylactic treatment of these immunocompromised patients can be used to avoid substantial morbidity. Patients undergoing immunosuppressive therapy and young children with insufficiently developed immune systems may likewise benefit from treatment with protease inhibitors to prevent, control, or eradicate infections caused by *C. parvum*. Further, protease inhibitors may be used to treat immunocompetent subjects who are exposed to *C. parvum* for the purpose of therapeutically treating or preventing the infection.

The protease inhibitors of this invention may be used in conjunction with conventional anti-infective agents, antimicrobial agents, immunomodulators, and pharmaceutical preparations indicated for the treatment of symptoms associated with cryptosporidiosis. It is believed that the aforementioned medicinal agents may interact synergistically with the inhibitors of this invention, particularly in the treatment of immunocompromised patients that may otherwise succumb to this opportunistic infection and its morbid consequences.

The protease inhibitors to be administered according to the method of the present invention include, but are not limited to, bases and pharmaceutically acceptable salts (e.g. acid addition salts) thereof. Examples of pharmaceutically acceptable acid addition salts include salts of inorganic acids such as sulfuric, nitric, phosphoric, and hydrochloric acid, as well as organic acids such as acetic, propionic, succinic, fumaric, maleic, citric, tartaric, cinnamic, lactic, mandelic, and ethanedisulfonic acid. The salts may be made by reacting the free base of the particular protease inhibitor with the chosen acid in a stoichiometric ratio in an appropriate solvent. The salts may be used, for example, in the preparation of oral and injectable formulations containing protease inhibitors as an active ingredient.

Oral and injectable formulations to be used according to the method of the present invention may also be microencapsulated or otherwise incorporated into a pharmaceutical dosage form in order to protect the protease inhibitors from unwanted biodegradation processes or to create a sustained-release effect. Oral preparations may also be enteric coated to protect the protease inhibitors from acids and enzymes created in portions of the gastrointestinal tract.

In another form of this invention there is provided a method for the treatment of infections with *C. parvum* in a mammal which comprises administering to the mammal a therapeutically effective amount of a serine protease inhibitor. The serine protease inhibitors target a specific biochemical component of the parasite in one or more of its developmental stages. Thus, the anticryptosporidial potential can be tailored to recognize proteolytic enzymes that are specific for the invading pathogen or that affect specific functional and developmental stages in the invading parasite's cycle. This course of action has proven clinically efficacious with regard to treatment of infection with HIV as well as the protozoan parasite Plasmodium species (i.e., etiologic agent of malaria).

A preferred serine protease inhibitor to be used in accordance with the present invention is alpha-1-antitrypsin ("AAT"). AAT used is a human alpha-1-antitrypsin purified from plasma (available in research-grade purity from Chemicon International, Inc., Temecula, Calif.). A pharmaceutical preparation of human AAT proteinase inhibitor, manufactured by Miles, Inc. under the trademark PROLASTIN, is commercially available and has been approved by the Food and Drug Administration for use as a supplement for human patients with congenital AAT deficiencies. Other preferred serine protease inhibitors to be used include aprotinin (available from ICN Biochemicals, Inc., Aurora, Ohio), soybean trypsin inhibitor ("SBTI") (available from Calbiochem-Novabiochem Corp., La Jolla, Calif.), and phenylmethylsulfonyl flouride ("PMSF") (available from Sigma Chemical Co., St. Louis, Mo.). Other serine protease inhibitors, such as methoxysuccinyl-ala-ala-pro-valine chloromethylketone ("MAAPVCK"), can also be used, but may require higher concentrations for adequate protease inhibition. Pharmaceutically or therapeutically effective amounts of these compounds are already know or can be determined by one of skill in the art, but are generally amounts sufficient to interfere with the reproduction and/or infectivity of *C. parvum*).

In yet another form of the invention, a method is provided for the treatment of infections with *C. parvum* in animals which comprises administering to an animal a therapeutically effective amount of an agent that inhibits both cysteine protease and serine protease. The cysteine/serine protease inhibitors which may be used in accordance with the invention include leupeptin (available from Calbiochem-Novabiochem Corp., La Jolla, Calif.), L-trans-epoxysuccinyl-leucylamindo-(4-guanidino)-butane ("E-64"), and/or antipain (available from ICN Biochemicals, Inc., Aurora, Ohio).

Preferred protease inhibitors to be orally administered include those that are not protein-based such as antipain, MAAPVCK, and PMSF. These non-protein protease inhibitors are less susceptible to proteolysis by non-target proteinases which are found primarily in the stomach. Administration of pH-sensitive protease inhibitors can be accomplished by employing several methods to reduce acid hydrolysis in the stomach. These methods include the use of enteric coating, microencapsulation, lipid encapsulation, or administration of a buffer agent (e.g., with antacids) prior to, or concomitantly with, the administration of a formulation containing the protease inhibitor.

The invention also includes a method of making pharmaceutical dosage forms containing a protease inhibitor for use in treating or preventing cryptosporidiosis.

Having now generally described the invention, the same will be further described by reference to certain specific examples which are provided herein for purposes of illustration only and which are not intended as limiting.

EXAMPLES

Example I

Preparation of C. parvum in Cell Culture

C. parvum (bovine isolate) oocysts used in this study were originally donated by the U.S. Department of Agriculture, Ames, Iowa. The oocysts were isolated from calf manure, preserved in 2.5% potassium dichromate, and used within 3 months of purification. Oocysts were decontaminated by suspension in 20% (vol/vol) 1.05% sodium hypochlorite on ice for 20 minutes. Oocysts were then washed three times in Hanks' balanced salt solution ("HBSS") and once in RPMI 1640 (available from Sigma, St. Louis, Mo.). Release of sporozoites was achieved by incubating oocysts in an excystation solution consisting of 0.25% (wt/vol) trypsin (available from Sigma, St. Louis, Mo.) and 0.75% (wt/vol) taurodeoxycholic acid (available from Sigma) in HBSS. The resulting suspension was incubated at 37° C. for 45 minutes and microscopically observed to confirm sporozoite release. Sporozoites were completely separated from intact oocysts and oocyst walls by passage through sterile polycarbonate filters (3 micron pore size, available from Millipore Corp., Bedford, Mass.) twice prior to inoculation of bovine fallopian tube epithelial ("BFTE") cell monolayers.

Primary BFTE cell cultures were prepared from bovine fallopian tubes (FT). Fat was trimmed from the serosal surfaces, mucus was gently squeezed from the lumens, and FT were decontaminated by being submerged in 70% ethanol for 30 seconds. The FT were then transferred to sterile culture petri dishes containing HBSS and washed twice. The BFTE cells were harvested either by flushing the FT with HBSS, using a 10 ml syringe equipped with a mouse feeding needle, or by opening the FT lengthwise with scissors and scraping the mucosal surfaces. The BFTE cells were subsequently washed in HBSS by centrifugation at 200×g (force of gravity) for 10 minutes, planted in 75-cm$^2$ flasks containing RPMI 1640 and cultured in a 5% $CO_2$ incubator at 37° C. for 72 to 120 hours. When the cell lines reached confluency, they were trypsinized, split, and planted onto cover slips positioned on the bottoms of individual wells in 24-well tissue culture plates. When cells reached 80% confluency, they were inoculated with either $10^5$ oocysts or $4 \times 10^5$ sporozoites per well. Plates were then maintained at 37° C. in a candle jar environment (17% $O_2$, 3% $CO_2$, 80% $N_2$). Growth medium was changed in each well every 72 hours. In wells inoculated with oocysts, the medium was first changed at 24 hours to remove any unexcysted oocysts.

Coverslips were removed at 5, 24, 48, 72, 96, and 120 hours from the inoculated wells containing monolayers of BFTE cells. The coverslips were washed in RPMI 1640, fixed in 100% methanol for 10 minutes, stained with Giemsa stain for 1 hour, and washed three times with double-distilled water ($ddH_2O$). Coverslips were then mounted on glass slides and examined under oil immersion (1000X), using bright-field microscopy. Parasites were enumerated by counting all developmental stages of C. parvum present in a single scan (67 fields) through the center of each coverslip. The data were statistically compared for significance, using analysis of variance (Fischer's protected least-significant-difference test using a "STATVIEW" statistical analysis application developed by Abacus Concepts, Inc., Berkeley, Calif.).

Successful infections were observed in BFTE cells inoculated with both oocysts and purified sporozoites. Parasites developed at the microvillous surface of BFTE cells in an intracellular but extracytoplasmic location. Significantly, multiple infections were common in individual cells, similar to those frequently observed in vivo.

To confirm the production of infective oocysts in cell culture, an immunosuppressed mouse model for cryptosporidiosis was used. Three groups of adult female C57BL/6N mice (6 weeks of age, each weighing 14 to 16 grams, purchased from Taconic, Germantown, N.Y.) were immunosuppressed with dexamethasone phosphate (available from Sigma, St. Louis, Mo.) provided in drinking water at a dosage level of 12 µg/ml. At 120 hours post-inoculation, coverslips from individual 24-well plates were collected, and the surfaces were scraped and pooled for each plate. All mice in a group were gavaged on day 7 immunosuppression with an equal volume of the resulting cells, cell products, and parasites (plate product) harvested from a single plate. Group 1 (four mice) and group 2 (five mice) received the plate product from plates inoculated with oocysts and sporozoites, respectively. Group 3 (five mice) was treated the same as group 1 except that the plate product was first suspended in 70% ethanol for 10 minutes to kill all stages of C. parvum except the oocysts. Fecal samples were collected from recta each day from mice in all groups and monitored for oocyst shedding, using oocyst-specific monoclonal antibody-based indirect immunofluorescence assay. Oocysts produced in BFTE cell culture were infective for immunosuppressed adult female mice. Also tested were 2 additional groups infected with non-cell culture derived oocysts. For further details on the complete experiment, see Yang et al., Infection and Immunity 64:349–354 (January 1996), the contents of which are incorporated by this reference.

Example II

Anticryptosporidial Effect of Alpha-1-Antitrypsin

The anticryptosporidial potential of the protease inhibitor AAT was evaluated in a BFTE cell culture system inoculated with C. parvum oocysts in accordance with the methods detailed in Example I. AAT concentrations of 5, 10, 50 100, and 500 micrograms per milliliter ("µg/ml") in RPMI medium were mixed with C. parvum oocysts and used to inoculate BFTE cell monolayers. At 24 hours post-inoculation, the BFTE cells were rinsed with RPMI medium, fixed in methanol, and stained with Giemsa. Parasites were enumerated in cell monolayers by brightfield microscopy. Results, as set out in Table 1, represent the mean number of parasites counted per treatment group expressed as a percent, plus or minus the standard deviation, of the mean number of parasites counted in the infection control group.

TABLE 1

| AAT Concentration (µg/ml) | Control Percent Survival |
| --- | --- |
| 0 (Control Group) | 100% |
| 5 | 49.1 +/− 3.8% |
| 10 | 43.9 +/− 4.2% |
| 50 | 42.7 +/− 1.6% |
| 100 | 30.4 +/− 1.9% |
| 500 | 14.7 +/− 6.3% |
| 1000 | 1.8 +/− 0.4% |

These results show a concentration-dependent reduction in the number of surviving parasites, compared to infection control mean populations, following treatment with AAT.

Significant reduction (P<0.001) in parasite numbers were shown at concentrations as low as 5–10 µg/ml. Not surprisingly, the most dramatic reduction in surviving parasite numbers were obtained with an AAT concentration of 1000 µg/ml. During microscopic enumeration of parasites in BFTE cell monolayers treated with AAT, intact (i.e. unexcysted) oocysts were frequently observed. This observation was predominantly associated with AAT concentrations exceeding 100 µg/ml. There was no evidence of cytotoxicity for BFTE cells at the AAT concentrations evaluated in this study.

Example III

Anticryptosporidial Effect of ANTIPAIN

The anticryptosporidial potential of the protease inhibitor ANTIPAIN was evaluated in a BFTE cell culture system inoculated with C. parvum oocysts utilizing the same methods and protease inhibitor concentrations as in Example II. Trial and data results are summarized in Table 2.

TABLE 2

| ANTIPAIN Concentration (µg/ml) | Control Percent Survival |
| --- | --- |
| 0 (Control Group) | 100 |
| 5 | 67.7 +/– 7.2 |
| 10 | 53.1 +/– 5.8 |
| 50 | 42.1 +/– 6.1 |
| 100 | 20.9 +/– 2.2 |
| 500 | 15.6 +/– 1.4 |
| 1000 | 6.6 +/– 1.4 |

These results show a concentration-dependent reduction in the number of surviving parasites, compared to infection control mean populations, following treatment with ANTIPAIN. Significant reduction (P<0.001) in parasite numbers were seen at concentrations as low as 5–10 µg/ml, with the most dramatic reduction in surviving parasite numbers being obtained with an ANTIPAIN concentration of 1000 µg/ml. During microscopic enumeration of parasites in BFTE cell monolayers treated with ANTIPAIN, intact (i.e. unexcysted) oocysts were frequently observed. This observation was predominantly associated with ANTIPAIN concentrations exceeding 100 µg/ml. There was no evidence of cytotoxicity for BFTE cells at the ANTIPAIN concentrations evaluated in this study.

Example IV

Anticryptosporidial Effect of APROTININ

The anticryptosporidial potential of the protease inhibitor APROTININ was evaluated in a BFTE cell culture system inoculated with C. parvum oocysts utilizing the same methods and protease inhbitor concentrations as in Example II. Trial and data results are summarized in Table 3.

TABLE 3

| APROTININ Concentration (µg/ml) | Control Percent Survival |
| --- | --- |
| 0 (Control Group) | 100 |
| 5 | 83.9 +/– 6.6 |
| 10 | 54.2 +/– 6.0 |
| 50 | 36.1 +/– 4.7 |
| 100 | 16.8 +/– 5.1 |

TABLE 3-continued

| APROTININ Concentration (µg/ml) | Control Percent |
| --- | --- |
| 500 | 10.9 +/– 4.7 |
| 1000 | 9.4 +/– 1.8 |

These results show a concentration-dependent reduction in the number of surviving parasites, compared to infection control mean populations, following treatment with APROTININ. As seen in previous examples, significant reduction (P<0.001) in parasite numbers were shown at concentrations as low as 5–10 µg/ml, with the greatest reduction in surviving parasite numbers were obtained with an APROTININ concentration of 1000 µg/ml. During microscopic enumeration of parasites in BFTE cell monolayers treated with APROTININ, intact oocysts were frequently observed. This observation was predominantly associated with APROTININ concentrations exceeding 100 µg/ml. There was no evidence of cytotoxicity for BFTE cells at the APROTININ concentrations evaluated in this study.

Example V

Anticryptosporidial Effect of Leupeptin

The anticryptosporidial potential of the protease inhibitor Leupeptin was evaluated in a BFTE cell culture system inoculated with C. parvum oocysts utilizing the same methods and protease inhibitor concentrations as in Example II, except that a 1000 µg/ml concentration was not included. Trial and data results are summarized in Table 4.

TABLE 4

| Leupeptin Concentration (µg/ml) | Control Percent Survival |
| --- | --- |
| 0 (Control Group) | 100 |
| 5 | 89.1 +/– 5.4 |
| 10 | 64.8 +/– 12.0 |
| 50 | 58.7 +/– 11.2 |
| 100 | 51.9 +/– 4.6 |
| 500 | 43.4 +/– 6.6 |

These results show a concentration-dependent reduction in the number of surviving parasites, compared to infection control mean populations, following treatment with Leupeptin. The number of parasites were significantly reduced (P<0.01) following treatment with Leupeptin at concentrations of 10 µg/ml and 50 µg/ml. Greater reductions of surviving parasites were observed at Leupeptin concentrations of 100 µg/ml and 500 µg/ml.

Example VI

Anticryptosporidial Effect of Soybean Trypsin Inhibitor

The anticryptosporidial potential of the protease inhibitor SBTI was evaluated in a BFTE cell culture system inoculated with C. parvum oocysts utilizing the same methods and protease inhibitor concentrations as in Example II, except that a 1000 µg/ml concentration was not included. Trial and data results are summarized in Table 5.

TABLE 5

| SBTI Concentration (μg/ml) | Control Percent Survival |
|---|---|
| 0 (Control Group) | 100 |
| 5 | 89.1 +/- 5.4 |
| 10 | 64.8 +/- 12.0 |
| 50 | 58.7 +/- 11.2 |
| 100 | 51.9 +/- 4.6 |
| 500 | 43.4 +/- 6.6 |

These results show a concentration-dependent reduction in the number of surviving parasites, compared to infection control mean populations, following treatment with SBTI. The number of parasites were significantly reduced ($P<0.01$) following treatment with SBTI at concentrations of 50 μg/ml and 100 μg/ml. A greater reduction of surviving parasites was observed at an SBTI concentration of 500 μg/ml.

Example VII

Anticryptosporidial Effect of Phenylmethylsulfonyl Flouride

The anticryptosporidial potential of the protease inhibitor PMSF was evaluated in a BFTE cell culture system inoculated with C. parvum oocysts in accordance with the methods detailed in Example I. PMSF concentrations of 1, 2, and 3 mM in RPMI medium were mixed with C. parvum oocysts and used to inoculate BFTE cell monolayers. The same methods of preparation and enumeration were used as in Example II. Trial and data results are summarized in Table 6.

TABLE 6

| PMSF Concentration (mM) | Control Percent Survival |
|---|---|
| 0 (Control Group) | 100 |
| 1 | 68.9 +/- 5.2 |
| 2 | 55.9 +/- 4.7 |
| 3 | 40.0 +/- 8.3 |

These results show a concentration-dependent reduction in the number of surviving parasites, compared to infection control mean populations, following treatment with PMSF. The number of parasites were significantly reduced ($P<0.001$) following treatment with PMSF at a concentration of 3 mM. Significantly greater reduction in surviving parasites was observed at PMSF concentrations of 2 mM and 3 mM.

Example VIII

Anticryptosporidial Effect of MAAPVCK

The anticryptosporidial potential of the protease inhibitor MAAPVCK was evaluated in a BFTE cell culture system inoculated with C. parvum oocysts utilizing the same methods and protease inhibitor concentrations as in Example II, except that a 1000 μg/ml concentration was not included. Trial and data results are summarized in Table 7.

TABLE 7

| MAAPVCK Concentration (μg/ml) | Control Percent Survival |
|---|---|
| 0 (Control Group) | 100 |
| 5 | 89.1 +/- 5.4 |

TABLE 7-continued

| MAAPVCK Concentration (μg/ml) | Control Percent Survival |
|---|---|
| 10 | 64.8 +/- 12.0 |
| 50 | 58.7 +/- 11.2 |
| 100 | 51.9 +/- 4.6 |
| 500 | 43.4 +/- 6.6 |

These results show a concentration-dependent reduction in the number of surviving parasites, compared to infection control mean populations, following treatment with MAAPVCK. The number of parasites were significantly reduced ($P<0.01$) following treatment with MAAPVCK at a concentration of 500 μg/ml.

Example IX

Combined in vitro anticryptosporidial activities of AAT and paromomycin

The anticryptosporidial potential of the protease inhibitor AAT in combination with the aminoglycoside paromomycin was evaluated in BFTE cell cultures. Each compound was tested at two different concentrations; AAT was evaluated at 250 μg/ml and at 500 μg/ml in combination with either 400 μg/ml or 1200 μg/ml of paromomycin. Purified oocysts ($10^5$) were mixed with various combinations of the two compounds and 1.0 ml of the resulting mixtures were used to inoculate confluent monolayers of BFTE cells on glass coverslips. Inoculated BFTE cells were maintained in a candle-jar environment at 37° C. for 24 hours. After 24 hours incubation, inoculated cell monolayers were rinsed with sterile RPMI 1640 medium to remove residual inoculum and either collected (24 hour treatment group) or incubated at 37° C. for an additional 24 hours (48 hour treatment group) or 48 hours (72 hour treatment group). The remaining steps of the inoculation procedure were conducted in accordance with the methods detailed in Example I. Trial and data results are summarized in Table 8.

TABLE 8

| AAT Conc. (μg/ml) | Paromomycin Conc. (μg/ml) | Control Percent Survival |
|---|---|---|
| 0 (Control Group) | 0 (Control Group) | 100 |
| 250 | 400 | 19.6 (@ 24 hrs) |
| | | 34.8 (@ 48 hrs) |
| | | 29.5 (@ 72 hrs) |
| 500 | 400 | 6.3 (@ 24 hrs) |
| | | 10.9 (@ 48 hrs) |
| | | 8.2 (@ 72 hrs) |
| 250 | 1200 | 8.0 (@ 24 hrs) |
| | | 4.3 (@ 48 hrs) |
| | | 1.6 (@ 72 hrs) |
| 500 | 1200 | 3.6 (@ 24 hrs) |
| | | 4.3 (@ 48 hrs) |
| | | 3.3 (@ 72 hrs) |

The number of parasites counted in a single scan across the diameter of a coverslip was significantly reduced ($P<0.01$) by each combination of AAT and paromomycin evaluated. The treatment group consisting of the highest concentrations of the two compounds (500 μg/ml AAT and 1200 μg/ml paromomycin) had the greatest quantitative effect on C. parvum infection for the 24 and 48 hour treatment groups evaluated.

Although the invention has been described in detail with respect to use of specific protease inhibitors, methods of treating infections caused by *C. parvum*, it should be realized that certain modifications can be made within the scope and spirit of the invention by those skilled in the art.

What is claimed is:

1. A method of treating cryptosporidiosis in a mammal which comprises administering to said mammal a serine protease inhibitor in an amount sufficient to interfere with the reproduction and infectivity of *Cryptosporidium parvum.*

2. The method of claim 1 wherein said mammal is immunocompromised.

3. The method of claim 1 wherein said mammal is a human.

4. The method of claim 3 wherein said human has been infected with a human immunodeficiency virus.

5. The method of claim 1 wherein said serine protease inhibitor is alpha-1-antitrypsin.

6. The method of claim 1 wherein said serine protease inhibitor is aprotinin.

7. The method of claim 1 wherein said serine protease inhibitor is soybean trypsin.

8. The method of claim 1 wherein said serine protease inhibitor is phenylmethylsulfonyl flouride.

9. The method of claim 1 wherein serine protease inhibitor is leupeptin.

10. The method of claim 1 wherein said serine protease inhibitor is antipain.

11. The method of claim 1 wherein said serine protease inhibitor is administered to said mammal parenterally.

12. The method of claim 1 wherein said protease inhibitor is L-trans-epoxysuccinyl-leucylamindo-(-guanidino)-butane.

13. The method of claim 1 wherein said serine protease inhibitor is administered to said mammal by parenteral route in microencapsulated form.

14. The method of claim 1 wherein said serine protease inhibitor is administered to said mammal orally.

15. A method of preventing cryptosporidiosis in a mammal which comprises administering to said mammal a serine protease inhibitor in an amount sufficient to prevent reproduction and infectivity of *Cryptosporidium parvum* in said mammal.

16. A method of treating cryptosporidiosis in a mammal which comprises administering to said mammal a protease inhibitor selected from the group of protease inhibitors consisting of alpha-1-antitrypsin, aprotinin, soybean trypsin, L-trans-epoxysuccinyl-leucylamindo-(4-guanidino)-butane and mixtures thereof in an amount sufficient to interfere with the reproduction and infectivity of *Cryptosporidium parvum.*

17. The method of claim 16 wherein said mammal is immunocompromised.

18. The method of claim 16 wherein said mammal is a human.

19. The method of claim 16 wherein said protease inhibitor is administered to said mammal parenterally.

20. The method of claim 16 wherein said protease inhibitor is administered to said mammal orally.

* * * * *